United States Patent [19]

Hydro

[11] 4,249,025

[45] Feb. 3, 1981

[54] NOVEL PROCESS FOR SYNTHESIS OF A LIQUID IRRITANT, 1-METHOXYCYCLOHEPTRATRIENE

[75] Inventor: William R. Hydro, Bel Air, Md.

[73] Assignee: The United States of America as represented by the Secretary of the Army, Washington, D.C.

[21] Appl. No.: 903,642

[22] Filed: Apr. 28, 1978

[51] Int. Cl.$^3$ ............................................. C07C 41/06
[52] U.S. Cl. ..................................... 568/667; 424/339
[58] Field of Search ......................................... 568/667

[56] References Cited

U.S. PATENT DOCUMENTS 3,084,194  3/1963  ter Borg et al. ...................... 568/667

*Primary Examiner*—Leland A. Sebastian
*Attorney, Agent, or Firm*—Nathan Edelberg; Robert P. Gibson; Harold H. Card, Jr.

[57] ABSTRACT

An improved multi-step process for synthesizing the liquid irritant 1-methoxycycloheptatriene from tropylium tetrafluoborate the improvement comprising the step of using a polymerization/condensation inhibitor or retarder to minimize impurities and increase yield of the irritant product. Phenothiazine is the preferred polymerization inhibitor.

17 Claims, No Drawings

NOVEL PROCESS FOR SYNTHESIS OF A LIQUID IRRITANT, 1-METHOXYCYCLOHEPTRATRIENE

DEDICATORY CLAUSE

The invention described herein may be manufactured, used and licensed by or for the Government for governmental purposes without the payment to me of any royalty thereon.

BACKGROUND OF THE INVENTION

This invention relates to an improved process for preparing the liquid irritant agent 1-methoxycycloheptatriene.

The invention further relates to an improved process for preparing the irritant agent 1-methoxycycloheptatriene from tropylium tetrafluoborate through use of a polymerization/condensation inhibitor to increase the yield and purity of the agent.

The invention still further relates to a more rapid and efficient method for isomerization of 7-methoxycycloheptatriene to its isomer 1-methoxycycloheptatriene.

The existing processes for preparing 1-methoxycycloheptatriene basically consists of a three step synthesis wherein an aqueous solution of cycloheptatrienyl tetrafluoroborate (tropylium tetrafluoroborate) in methanol is first converted to the 7-methoxycyclohepta 1,3,5-triene isomer by reaction with sodium bicarbonate; the resulting 7-isomer is thermally isomerized to 3-methoxycyclohepta-1,3,5-triene and this 3-isomer is in turn is either thermally isomerized to 1-methoxycyclohepta-1,3,5-triene or isomerized in a methanol solution, under acid catalysis, to the 1-methoxycyclohepta-1,3,5-triene isomer. The prior art process which had given the best yield of 1-methoxycylohepta-1,3,5-triene, i.e, approximately 43% with a purity of 85–89 mole % is best illustrated schematically in the following series of three reaction equations;

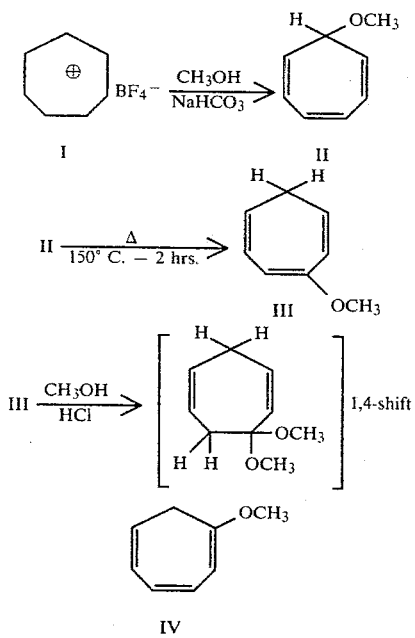

In the first step of the above synthesis, warm water is used to dissolve the cycloheptatrienyl tetrafluoborate (tropylium tetrafluoborate) (I) salt under a nitrogen atmosphere. Methanol is added to the resulting aqueous solution of (I), followed by the addition of solid sodium bicarbonate to give the reaction product 7-methoxycycloheptatriene (II). The 7-methoxycycloheptatriene (II) is isomerized by heating at 150° C. for two hours to produce 3-methoxycycloheptatriene (III). In the third step, 3-methoxycycloheptatriene (III) is isomerized in an acid catalyzed rearrangement utilizing hydrogen chloride in methanol at room temperature for two hours, followed by neutralization with sodium bicarbonate, filtration and fractional distillation to give the product 1-methoxycycloheptatriene (IV).

The prior art processes described above have resulted from numerous studies of the isomerization reaction of alkoxycycloheptatriene. The production of cycloheptatrienylium bromide, its hydrogenation to cycloheptane, its subsequent conversion by phenyllithium to 7-phenylcycloheptatriene and the synthesis of 7-methoxycyclohepta (1,3,5) triene was first disclosed in *The Cycloheptatrienyl (Tropylium) Ion.*, J. Am. Chem. Soc. 76, 3202 (1954) by W. Von E. Doering et al. Synthesis of 1-ethoxy-1,3,5-cycloheptatriene by reaction of 1-ethoxycyclohexene with dichlorocarbene and hot quinoline rearrangement is shown in *A Synthesis of 3,5-Cycloheptadienone* by W. E. Parham et al, J. Am. Chem. Soc. 84, 1755 (1962). Irradiation of 7-methoxycyclohepta-1,3,5-triene in the vapor phase has given a 40% yield of 1-methoxycyclohepta-1,3,5 triene by the process of O. L. Chapman et al, *An Anomalous Photoisomerization in the Cycloheptatriene Series,* Proc. Chem. Soc. at 221, July 1963.

Thermal isomerization of 7-methoxycycloheptatriene at 150° C. by irreversible reaction into 3-methoxycycloheptatriene and subsequent reversible isomerization of the 3-isomer to 1-methoxycycloheptatriene under the same conditions is disclosed in *Thermal Isomerization of Alkoxycycloheptatriene,* Proc. Chem. Soc., February 1964, 59 by E. Weth et al, and A. Piter Borg et al, *The Chemistry of Cycloheptatriene Part XII: The Thermal Behaviour of Substituted Cycloheptatrienes,* Rec. Trav. Chim. 84, 1230 (1965). Thermal isomerization of alkoxycycloheptatrienes, e.g., 7-methoxycycloheptatriene in sealed tubes at temperatures in the range of 75°–220° C., i.e., under pressure to give a mixture of 3-methoxy-1-methoxy and 2-methoxy-cycloheptatriene is disclosed in T. Nozoe et al, *The Thermal Isomerization of Alkoxycycloheptatrienes and Some Reactions of its Product,* Bull Chem. Soc. of Japan, 38, 665-674, April 1965. T. Tezuka et al disclosed in *Thermal Reactions of Alkoxycycloheptatriene at 300°–800° C.,* Chem. Lett. Japan, pp 1341-1346 (Chemical Society of Japan), 1974, that 7-methoxycycloheptatriene is completely consumed at 300°–400° C. to form 3-methoxy and 1-methoxycycloheptatrienes when pyrolyzed by passing through a quartz column containing heated quartz tips. Heating at 450° gave 1-methoxycycloheptatriene as the sole isomer product.

Finally, the prior art has recognized the benefit of excluding moisture from the thermal isomerization reaction of 7-methoxycycloheptatriene to the 3-methoxy and subsequently rearrangement to the 1-methoxy isomer by conducting the reaction at 150° C. for 2.5 hr in a nitrogen atmosphere.

In all the above described methods of preparing the irritant 1-methoxycycloheptatriene, yields at each step are adversely effected by high-boiling polymeric or condensation-type material recovered as pot residue after distillation of the crude product. The overall yield of product and the purity of the product 1-isomer has been limited. Applicant's process has succeeded in obtaining significantly better yields of higher purity product through elimination of the adverse effects of these high boiling polymeric materials.

SUMMARY OF THE INVENTION

An improved multi-step process for synthesizing the liquid irritant 1-methoxycycloheptatriene through the steps of reacting cycloheptatrienyl tetrafluoroborate in aqueous solution with methanol and sodium bicarbonate to produce 7-methoxycycloheptatriene, thermally isomerizing the 7-methoxycycloheptatriene to 3-methoxycycloheptatriene by heating at 150° C. for 2 hours and isomerizing the 3-methoxycycloheptatriene to 1-methoxycycloheptatriene by acid, catalyzed rearrangement employing methanolic hydrogen chloride followed by neutralization with sodium bicarbonate, filtration and fractional distillation to give the final product the improvement comprising the step of utilizing a polymerization/condensation inhibitor to increase the overall yield and purity of the 1-methoxycycloheptatriene product. The overall yield and purity of the product can further be increased through the step of conducting the thermal isomerization of 7-methoxy to 3- and 1-methoxycycloheptatriene at 180° C. under reduced pressure, e.g., by heating in a sealed reactor.

It is the principal object of this invention to provide an improved process for synthesizing the liquid irritant 1-methoxycycloheptatriene through use of a high-boiling polymerization/condensation material inhibitor.

It is a further object of this invention to provide an improved process for synthesizing an alkoxycycloheptatriene isomer product of increased overall yield and purity.

It is a still further object of this invention to provide an improved process for more rapidly synthesizing a 1-alkoxycycloheptatriene, e.g., 1-methoxycycloheptatriene in increased overall yield and purity through the step of increasing the thermal isomerization of the 7-isomer to the 1-isomer by heating at 180° C. under reduced pressure.

These and other objects of this invention will become apparent from the following detailed description of the invention.

DESCRIPTION OF THE INVENTION

The improved process of this invention for synthesizing the liquid irritant 1-methoxycycloheptatriene in substantially increased yields and purity involves the novel use of a polymerization inhibitor/retarder in the prior art process described above. The polymerization inhibitor/retarder of this invention minimizes formation of high-boiling polymeric or condensation-type material, which had previously remained as impurities in the crude product and pot residue. This minimization of high-boiling polymeric material has resulted in substantially increased yields of 1-methoxycycloheptatriene, i.e., from approximately 43% yield without inhibitor to 62%–69% with the inhibitor and a purity increase from the range 85–89 mole % to the range of 92–93.6 mole % with the instant improved process.

The polymerization inhibitor/retarders that have been found to have utility in the process of this invention include phenothiazine, hydroquinone, nitrobenzene and L-ascorbyl palmitate, with phenothiazine being preferred as producing the greatest increase in product yield and purity. A more complete discussion of the scope of compounds which are recognized in the art as polymerization inhibitor/retarder, together with a detailed discussion of the mechanism by which polymerization is suppressed, can be found in the text *Principles of Polymerization* by George Odian, McGraw-Hill, Inc., 1970 at pp. 221–231.

The polymerization inhibitor has produced increased yields and purity of the final 1-methoxycycloheptatriene product when added during the first step of the process, but optimum results are obtained when the inhibitor is present during each reaction step in the multi-step synthesis process, e.g., by addition prior to each reaction step.

The improved process of this invention also includes other modifications of the prior art process which increase yield and purity of the instant product, particularly when used with the polymerization inhibitor of this invention. In particular, it has been found that by heating the water, which is added to the cycloheptatrienyl tetrafluoroborate salt in step 1 of the process, to approximately 52° C. under nitrogen atmosphere and purging the water with nitrogen for 30 minutes prior to addition of said tetrafluoroborate salt, a significant increase in yield of the 7-isomer is achieved and consequently, a greater yield of 1-iosmer product results at increased reaction rates. Replacement of the sodium bicarbonate with triethylamine in the acid catalyzed rearrangement of step 3 also decrease overall reaction time by instantaneous neutralization of the acid.

The preferred embodiment of the improved process of this invention involves the use of the above mentioned process modifications of the prior art process, particularly the use of the polymerization inhibitor phenothiazine, with the additional process improvement of heating the 7-methoxycycloheptatriene in the second step of the process to an elevated temperature, e.g., 180° C. at reduced pressure to give a final product 1-methoxycycloheptatriene of increased mole percent yield and purity. More specifically, it has been found that when 7-methoxycycloheptatriene is heated at 180° C. under reduced pressure, a substantial quantity of the order of 80 mole % of 7-isomer is isomerized to 1-methoxycycloheptatriene with complete consumption of the 7-isomer whereas heating at 150° C. (atmosphere pressure), as in the prior art process, yields the 3-methoxycycloheptatriene as a major component with only approximately 12–13 mole % 1-methoxycycloheptatriene product. Subsequent acid catalyzed rearrangement (step 3 of the synthesis) of the product in the preferred process yields a final product containing approximately 92 mole % of the 1-methoxy isomer and a purity of methoxy isomers of 99 mole % versus a yield of 90 mole % 1-methoxy isomer (96% purity of methoxy isomer) obtained when the improved process of this invention utilizes the atmospheric heating at 150° C. of the prior art process.

The improved process of this invention can be best illustrated by reference to the reaction equation for the preferred embodiment of the instant improved process.

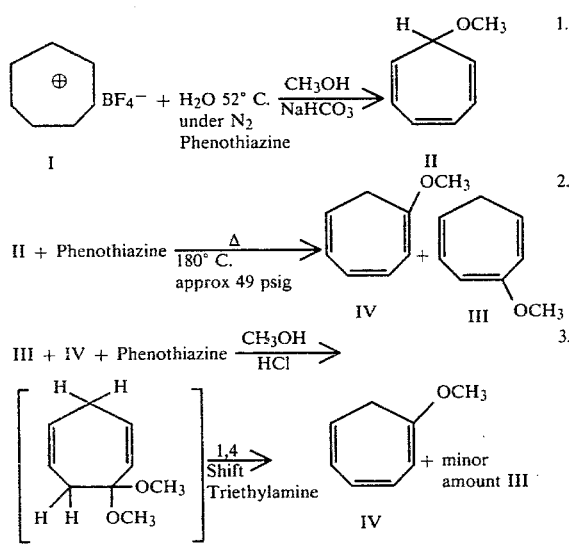

In the above process, water was heated to 52° C. and purged with nitrogen to expel any dissolved oxygen. Phenothiazine was added, followed by addition of cycloheptatrienyl tetrafluoborate (I), methyl alcohol and solid sodium bicarbonate to give a crude product, 7-methoxycycloheptatriene (II), which was distilled in the presence of phenothiazine to give a yield of approximately 59%. The 7-methoxycycloheptatriene with added phenothiazine inhibitor, is then thermally isomerized by heating at 180° C. under pressure, e.g., in a sealed reaction vessel, to give a 100% conversion to a product, containing 1-methoxycycloheptatriene (IV) as its major component, e.g., 82 mole % and minor amounts of 3-methoxy isomer, e.g., 16 mole % and 2-methoxycycloheptatriene isomer, with added phenothiazine, is treated with methanolic hydrogen chloride for 2 hours at room temperature, followed by neutralization with triethylamine, filtration, and fractional distillation to effect acid catalyzed rearrangement of the 3-methoxy isomer to 1-methoxycycloheptatriene. The final product contained approximately 92 mole % 1-methoxycycloheptatriene, 2 mole % 3-isomer and 5 mole % of 2-methoxycycloheptatriene, with an overall methoxy isomer purity of 99%. The preferred process exhibited at approximate 70–75% yield of 1-methoxycycloheptatriene from the initial 7-isomer, which is significantly greater than the best prior art yield of approximately 43% and an improvement over the instant process of using phenothiazine with atmospheric heating of the 7-isomer at 150° C. (approximately 62–67%).

The improved process of this invention can be best shown by the following detailed examples, which are meant to be merely illustrative and not limiting upon the invention.

EXAMPLE 1

Preparation of 1-methoxycyclohepta-1,3,5-triene utilizing phenothiazine as a polymerization inhibitor

Step A. Preparation of 7-methoxycyclohepta-1,3,5-triene

In a 3-liter, 3-neck, round-bottom flask equipped with a stirring bar, thermometer, and gas inlet tube, 1200 ml of water was heated to 52° C. and purged with nitrogen to expel any dissolved oxygen. A solution of 0.53 gm of phenothiazine (0.1% by weight of reactant cycloheptatrienyl tetrafluoroborate) in 25 ml of benzene was added, followed by addition of 534 grams (3 moles) of cycloheptatrienyl tetrafluoroborate, during which time heat was reapplied until a temperature of 50° C. was attained. To the resulting solution was added 300 ml of methyl alcohol and stirring was discontinued. A resulting dark green solution was cooled to approximately 35° C., and 325 grams (3 moles) of solid sodium carbonate were added rapidly but cautiously in order to avoid excessive frothing.

The reaction mixture was transferred to a 2-liter separatory funnel, the upper oily layer separated, and the aqueous layer was extracted with five 200 ml portions of ethyl ether. The oily layer and combined ethereal extracts were dried over anhydrous magnesium sulfate and the solvent was removed in vacuo on a rotary evaporator. The crude yield of 332.4 grams (90.7% of theoretical yield) contained 76 mole % of 7-methoxycyclohepta-1,3,5-triene according to NMR analysis. Vacuum distillation of the crude product through a 6-inch, air-jacketed Vigreux column in the presence of 0.33 gram of phenothiazine (0.1% of crude product weight) at 15 mm Hg under a nitrogen atmosphere gave the four fractions listed below, with a combined weight of 216.2 gm representing a 59.0% yield.

| Boiling Point | Fraction | Weight | Mole % Purity 7-Methoxycyclohepta-1,3,5-triene | Cyclohepta-1,3,5-triene |
|---|---|---|---|---|
| (°C./torr) | | (gm) | | |
| 25–56 | 1 | 20.0 | 73.0 | 27 |
| 56–60 | 2 | 85.3 | 98.5 | 1.5 |
| 59.5–60.5 | 3 | 66.2 | 99 plus | trace |
| 60.5–48 | 4 | 44.7 | 99 plus | trace |

Step B. Preparation of 3-methoxycyclohepta-1,3,5-triene

Phenothiazine (1.4 gm=0.1% by weight of 7-methoxycycloheptatriene) was dissolved in 1381.9 gm of distilled 7-methoxycycloheptatriene. The solution was then heated under nitroen at ambient pressure for 2 hours at 150° C., during which time low-boiling materials were removed by a condenser set for downward distillation. Upon cooling, the residual material weighed 1345.2 grams, representing a crude yield of 97.3% (based on initial 7-methoxy isomer). NMR analysis indicated a product composition of 76 mole % 3-methoxycyclohepta-1,3,5-triene, 12 mole % 1-methoxycyclohepta-1,3,5-triene and 4 mole % unconverted 7-methoxy isomer. The product was of sufficiently good quality to be utilized for conversion to 1-methoxycycloheptatriene without prior distillation.

Step C. Preparation of 1-methoxycyclohepta-1,3,5-triene

A solution of 360 ml (353.8 gm) of the crude 3-methoxycycloheptatriene from the above step, 0.35 gm of phenothiazine, 1750 ml of methyl alcohol, and 36.4 ml of methanolic hydrogen chloride (98.1 mg HCl/ml methyl alcohol solution) was stirred for 2 hr. 15 min. at ambient temperature under a nitrogen atmosphere. The clear, red-colored acidic solution was neutralized with 9.9 gm of triethylamine, the solvent was removed in vacuo on a rotary evaporator, and the residue was filtered through a fritted-glass funnel containing a layer of Celite filter aid. The resulting 342.4 gm (96.8% crude yield) of reddish-colored filtrate was indicated by NMR analysis to contain 60 mole % purity of 1-methoxycycloheptatriene.

Vacuum fractional distillation of the crude product at 5 mm Hg under a nitrogen atmosphere afforded a main fraction of 204.5 gm (57.8% yield, bp 43°–46.5°) of colorless distillate. NMR analysis indicated the distillate was 96.1 mole % in combined 1-methoxy and 3-methoxy isomers, and indicated a 90.7 mole % content of 1-methoxycycloheptatriene in the sample. A second fraction afforded 42.1 gm (11.9% yield) of colorless product which was 90.4 mole % pure in 1-, 2-, and 3-methoxy isomers and contained 51.2 mole % 1-methoxycycloheptatriene. The total yield of both fractions was 69.7% (based on crude reactant 3-methoxy isomer).

EXAMPLE 2

(A) Former process of preparing 7-methoxycyclohepta-1,3,5-triene and (B) said former process modified by addition of phenothiazine prior to distillation of crude 7-methoxy isomer (A) The procedure of Example 1, Step A, was repeated using one-third molar proportions but without the use of an inhibitor (phenothiazine in benzene solution). A crude 7-methoxy isomer (75.5% yield) was indicated by NMR analysis to contain 9 mole % cycloheptatriene, 9 mole % aromatic impurities, 3 mole % ethyl ether and 79 mole % 7-methoxy isomer. Distillation under a nitrogen atmosphere at 10 mm Hg afforded two fractions (47.2% yield based on the fluoborate reactant) which NMR indicated to contain 3 mole % cycloheptatriene and 97 mole % 7-methoxycycloheptatriene.

(B) A three-fold scale-up of the above procedure was conducted (80.6% yield of crude 7-methoxy isomer). Vacuum distillation at 10 mm Hg under a nitrogen atmosphere and with 0.29 gm of phenothiazine (0.1% of crude product weight) gave 183.9 gm (50.2% yield) of 7-methoxycycloheptatriene.

EXAMPLE 3

Acid catalyzed rearrangement of 3-methoxycyclohepta-1,3,5-triene to 1-methoxycycloheptatriene (A) without phenothiazine and (B) with phenothiazine added prior to distillation (A) 3-Methoxycycloheptatriene (56.0 gm) in a 1-liter 2 neck flask was diluted with 280 ml of methanol while under a nitrogen atmosphere. Methanolic hydrogen chloride (4.0 ml) containing 142.8 mg HCl/ml methanol was added and after stirring for 2 hr. 20 min., the resulting clear red colored solution was neutralized with 1.6 gm triethylamine, the solvents evaporated in vacuo on a rotating film evaporator, and filtered through a fritted glass funnel containing a layer of Celite yielding 45.3 gm (80.7% yield) of medium brown colored solution. NMR analysis revealed 50 mole % purity of 1-methoxycycloheptatriene. Distillation of this crude product at 5 mm Hg under a nitrogen atmosphere afforded 26.0 gm (46.4% yield) of 1-methoxycycloheptatriene (89.2 mole %, 97.1 mole % pure 1- and 3-methoxy isomers by NMR).

(B) The above reaction was repeated with 72 ml (69.6 gm) of distilled 3-methoxy isomer, 350 ml of methanol, 5 ml of methanolic hydrogen chloride, and neutralized with 2 gm of triethylamine. The resulting 64.9 gm of crude product was distilled with 0.06 gm of phenothiazine (0.1% of crude product weight) at 5 mm Hg under a nitrogen atmosphere to give 40.5 gm (58.2% yield) of colorless 1-methoxycycloheptatriene. NMR analysis of the product (2 fractions) indicated 97.0 and 98.2 mole % pure in 1- and 3-methoxy isomers containing 85.0 and 91.7 mole % 1-methoxycycloheptatriene, respectively. Redistillation in the presence of phenothiazine gave a 53.7% yield (37.4 gm, 94.9% recovery) of colorless 1-methoxy isomer (98.2 mole % pure in 1- and 3-methoxy isomers, 89.6 mole % 1-methoxycycloheptatriene by NMR analysis).

EXAMPLE 4

Preparation of 1-methoxycyclohepta-1,3,5-triene by Thermal Isomerization of 7-methoxycycloheptatriene under pressure Separately, 88.3 and 63.1 grams of 7-methoxycycloheptatriene with purities of 97.4 and 98.2 mole %, respectively, were transferred to a pear-shaped, heavy-walled, glass flask of 200 ml capacity. The void was filled with nitrogen, and the flasks were sealed with a neoprene gasket and glass stopper held in place with a fitted heavy-gauge wire brace. The flasks were then heated for 3 hours in an oil bath maintained at 180° C. After cooling, the flasks were opened and the product analyzed by NMR. The results are shown in the table below.

| | | Isomer Ratio | | | |
|---|---|---|---|---|---|
| Run | Weight (gm) | 1-Isomer | 3-Isomer | 2-Isomer | Total Isomers (mole %) |
| 1 | 88.3 | 77.0 | 18.6 | 4.4 | 97.0 |
| 2 | 63.1 | 81.2 | 13.2 | 5.5 | 95.8 |

A solution of methanol (1521 ml) containing 0.31 gm phenothiazine, 15 ml anhydrous methanolic hydrogen chloride (178.7 mg/ml), and 304.6 gms of 1-methoxycycloheptatriene (80 mole % pure), was stirred for 2 hours 20 minutes at ambient temperature. The acidic solution was then neutralized with 7.5 gm of triethylamine, the solvent was removed in vacuo on a rotary evaporator, and the residual liquid was filtered through a fritted-glass funnel (coarse porosity) containing a layer of Celite filter aid to give 269.0 grams of crude product. Washing of the filter cake with ether followed by removal of solvent from the filtrate gave an additional 20.7 grams of crude product. Both products were combined to give a crude yield of 95.1% containing 62 mole % of 1-, 2-, and 3-methoxy isomer. Vacuum fractional distillation of this product through a 6 inch, air-jacketed Vigreux column gave the fractions shown in the table below.

| Fraction | Boiling Point °C./5 torr | Weight (gm) | Yield (%) | 1-Methoxy Isomer | Total 1-,2-,3- Methoxy Isomer |
|---|---|---|---|---|---|
| 1 | 36–37 | 111.5 | 36.6 | 88.0 | 95.1 |
| 2 | 37–40 | 91.2 | 29.9 | 90.8 | 96.4 |
| 3 | 40–33 | 24.2 | 7.9 | 81.0 | 91.2 |

EXAMPLE 5

Preparation of 1-methoxycyclohepta-1,3,5-triene by thermal isomerization under pressure Five thermal-pressure reactions of distilled 7-methoxycycloheptatriene (132.8–136.7 gm of 83.7–100% purity) were carried out at 180° C. for 3 hours in the presence of 1% phenothiazine and over a nitrogen atmosphere in a 200 ml pear-shaped heavy walled glass bomb. NMR analysis indicated the mole percent purity of the 1-, 2-, 3-methoxy isomers was 90–96.5 and the mole percent purity of the 1-methoxy isomer was 66–77.

Upgrading of the above products by acid catalyzation gave 1-methoxycycloheptatriene of exceptionally high yield and purity. Thus, 0.36 gm of phenothiazine was added to 365 ml (358.0 gm) of methoxycycloheptatriene (ca. 94 mole % 1-, 2-, 3-methoxy isomer; 77 mole % 1-methoxy isomer) stirred in a nitrogen atmosphere, followed by 730 ml of A. C. S. certified methanol (2 ml methanol/ml methoxycycloheptatriene), and 18.3 ml of methanolic hydrogen chloride containing 121 mg HCl/ml methanol solution. After the solution was stirred for 2 hours 20 minutes, it was neutralized with 6.1 gm of triethylamine and the methanol was evaporated in vacuo from a rotating film evaporator. The product containing solid triethylamine hydrochloride was diluted with 250 ml ether, the mixture filtered through a fritted glass funnel, a layer of Celite filter acid, and the filter cake washed with ether. The ethereal solution was evaporated in vacuo again until a net weight of 364.2 gm was attained. High vacuum distillation of the medium red colored clear solution containing 0.36 gm of phenothiazine gave two fractions as shown below.

| Fraction | Weight (gm) | Mole % Purity 1-Isomer | Methoxycycloheptatriene Total 1-, 2-, 3-Isomer |
|---|---|---|---|
| I | 218.2 | 93.6 | 98.6 |
| II | 29.8 | 62.6 | 94.4 |

One percent BHA and BHT (butylated hydroxyanisole and toluene, respectively) were added to fraction I as light stabilizers. The combined weight of fractions I and II represent a yield of 69.2%.

Another upgrading of 353 ml (348.8 gm) of thermal-pressure reaction product as above by acid catalyzed rearrangement gave the following:

| Fraction | Weight (gm) | Mole % Purity 1-Isomer | 1-, 2-, 3-Isomer |
|---|---|---|---|
| I | 195.3 | 93.1 | 98.3 |
| II | 37.9 | 72.5 | 94.9 | which represented a total yield of 66.9%.

EXAMPLE 6

In a study of the thermal-pressure reaction of 7-methoxycycloheptatriene in an aluminum bomb (61.7 mm×19 mm cavity, 5 mm wall thickness, and 19 ml capacity), it was found that the pressure increased gradually and was dependent upon time and temperature. After 4 hours at 180°–188° C., the final pressure was 58 psig, after 1 hour at 220° C., the final pressure was 80 psig. The mole percent purity in each preparation was ca. 85 for 1-, 2-, 3-methoxy isomers and ca. 72 for 1-methoxycycloheptatriene. When heating at 220° C. was continued for an additional three hours, the pressure reached 118 psig and the product obtained, when analyzed by NMR, had a decreased mole percent purity of 1-, 2-, 3-methoxy isomers (ca. 64).

EXAMPLE 7

Comparison of thermal isomerization of 7-methoxycyclohepta-1,3,5-triene with phenothiazine inhibitor at 150° C. (atmosphere pressure) and 180° C. (greater than atmospheric pressure)

Heating 7-methoxycycloheptatriene at 150° C. and atmospheric pressure affords 3-methoxy isomer as the principal product whereas heating at 180° C. under pressure affords 1-methoxy isomer as the major component, as shown below.

| Method | 7-Isomer | 2-Isomer | 3-Isomer | 1-Isomer |
|---|---|---|---|---|
| I  150° C. (atmo) | 3.5 | — | 83.7 | 12.8 |
| II 180° C. (under pressure) | 0 | 5.5 | 13.2 | 81.2 |

Separate treatment of the products with methanolic hydrogen chloride (phenothiazine present during reaction and fractional distillation) gave the following results:

| Source of Starting Material | % Yield 90% (1-Isomer) | % Yield Less Pure (1-Isomer) | Total |
|---|---|---|---|
| I  (150° C., atm.) | 54.8 | 12.0 | 66.8 |
| II (180° C., press.) | 66.6 | 7.9 | 74.5 |

EXAMPLE 8

Comparison of thermal isomerization of 7-methoxycyclohepta-1,3,5-triene by heating in a sealed NMR tube at 180° C. with and without phenothiazine inhibitor One to two milliliters of a solution prepared by dissolving 0.32 gm of phenothiazine in 32.1 gm of 94 mole % purity 7-methoxy isomer were transferred to six NMR tubes over a nitrogen atmosphere and immersed in a pre-heated oil bath at 180° C. for the time indicated below, cooled to room temperature, and the NMR observed

| Time | 1-Isomer | 2-Isomer | 3-Isomer | 7-Isomer | 1-,2-,3-Isomer |
|---|---|---|---|---|---|
| 3 min | 2.5 | — | 56.2 | 41.3 | |
| 5 min | 5.4 | — | 72.8 | 21.7 | |
| 10 min | 14.3 | — | 78.6 | 7.1 | |
| 30 min | 36.9 | none | 60.9 | 2.2 | |
| 1 hr | 55.6 | 2.2 | 40.2 | 2.0 | |
| 2 hr | 69.9 | 6.8 | 23.3 | — | |
| 3 hr | 76.3 | 6.8 | 16.9 | — | |
| 4 hr | 76.3 | 8.4 | 15.3 | — | 87.6 |
| 5 hr | 77.4 | 7.3 | 15.4 | — | 89.0 |

The reaction was then carried out without an inhibitor in a pear-shaped heavy walled glass bomb of 200 ml capacity. In a first synthesis without an inhibitor, 88.3 gm of 97.4 mole % purity 7-methoxy isomer was employed. A 63.1 gm sample of 98.2 mole % 7-methoxy isomer was used in a second synthesis. The glass bombs were secured with a neoprene gasket and glass stopper held in place with a fritted heavy gauge wire brace.

| Run | Time | Mole Percent Methoxy Isomer Ratio 1-Isomer | 2-Isomer | 3-Isomer | Purity 1-, 2-, 3-Isomer |
|---|---|---|---|---|---|
| 1 | 3 hr | 77.0 | 4.4 | 18.6 | 97.0 |
| 2 | 3 hr | 81.2 | 5.5 | 13.2 | 95.8 |

As shown in the above examples, the instant process yields 7-methoxycycloheptatriene, 3-methoxycycloheptatriene and final product 1-methoxycycloheptatriene, respectively, in significantly increased amounts and purity over that obtained in prior art processes through use of "catalytic" amounts, i.e., 0.1–1.0% by weight of reactant mixture of phenothiazine polymerization condensation inhibitor. In particular, the addition of phenothiazine to crude 7-methoxycycloheptatriene prior to distillation increased the yield from 43.2% to 50.2%. When phenothiazine was added to water heated to 52° C. under nitrogen followed by addition of cycloheptatriene tetrafluoroborate, methanol and solid sodium bicarbonate, the yield of distilled 7-methoxycycloheptatriene was 59.0%.

The conversion of 7-methoxy isomer to the 3-methoxy isomer by thermal isomerization at 150° C. (atmospheric pressure) with phenothiazine inhibitor added prior to distillation gave an 86.6% yield of 3-methoxy isomer, whereas addition of phenothiazine prior to heat isomerization gave 97.3% yield of 3-methoxy isomer.

The initial conversion of 3-methoxy isomer to the 1-methoxy isomer without phenothiazine inhibitor gave a yield of approximately 46.4%. The yield was increased by use of phenothiazine during fractional distillation to 58.2% and the use of phenothiazine during the neutralization reaction and during fractional distillation gave a further increase in yield to 62.1%.

Finally, the conversion of 7-methoxy isomer to 1-methoxycycloheptatriene by thermal isomerization at 180° C. (under pressure) with use of phenothiazine as a polymerization inhibitor gave an increased final yield of 1-methoxycycloheptatriene of the order of 74.5%.

The methoxycycloheptatriene isomers used in the process of this invention are known to be susceptible to autoxidation, particularly the 1-methoxycycloheptatriene product which has customarily been stabilized with anti-oxidants. It is therefore essential that a nitrogen atmosphere be maintained during all steps of the instant process.

The most significant improvement in the improved process of this invention is the use of a polymerization inhibitor/retarder during all reaction and distillation steps of the instant process for minimizing the presence of impurities and extraneous materials in the crude methoxycycloheptatriene products and thereby increasing the final yield of 1-methoxycycloheptatriene product. Use of a concentration of approximately 0.1% w/w of the preferred phenothiazine inhibitor in all reaction steps has been found to give significantly improved yields, but this amount of phenothiazine inhibitor is not critical and can be varied within the skill of one in the art. As a practical matter, however, yields of 1-methoxy isomer have not been significantly improved by use of phenothiazine in amounts in excess of the present 0.1% w/w concentration.

The temperature of the fluoroborate solution is critical in the sense that when the temperature exceeds 60° C., product yield decreases. Further decreases in yield were noted if the crude 7-methoxy isomer product was allowed to stand for an extended period of time, e.g., overnight prior to distillation.

The reaction temperature used in the thermal isomerization of 7-methoxycycloheptatriene to 3-methoxycycloheptatriene at atmospheric pressure should not substantially exceed 150° C., since at higher temperatures, there is a potential for loss of material due to charring. When the thermal isomerization was carried out under pressure in a sealed container at 180° C., all of the 7-methoxy isomer was thermally isomerized to give 1-methoxycycloheptatriene as its principal product. The temperature used in the sealed container thermal isomerization can be increased above 180° C., e.g., 220° for one hour or 250° C. for 5 minutes without adversely affecting product yield, but continued heating at higher temperatures may result in decreased purity of the methoxycycloheptatriene isomer product.

The time requirement for the acid-catalyzed isomerization of 3-methoxycycloheptatriene to 1-methoxycycloheptatriene has been found to be 2 hours for optimum conversion, with shorter periods giving less conversion and larger periods resulting in increased impurity content in the final product. The ambient temperature conditions used in this acid-catalyzed rearrangement process step can be varied to give faster or slower reaction rates with higher or lower temperatures, but the overall yield and purity will not be significantly effected.

The acid-catalyzed isomerization reaction has been found to be sensitive to substantial reduction in the amount of acid catalyst used (almost no conversion with an 80% reduction in catalyst); but increasing the amount of catalyst, e.g., 100% increase, has no effect on the yield.

The use of triethylamine as a neutralizing agent in the acid catalyzed isomerization reaction has resulted in a more rapid and convenient reaction than that obtained with the anhydrous sodium bicarbonate of the prior art process.

With the above reaction condition limitations in mind, the reaction conditions and amounts of reactants used in the present process may be varied within the scope of the invention to achieve optimum yield and purity of product 1-methoxycycloheptatriene irritant agent.

The particular materials and apparatus used in the practice of this invention are conventional in the art and most are readily available from commercial suppliers. The particular apparatus used in the practice of this invention such as the 6 inch by 22-mm OD Vigreux columns used in distillation, are conventional and can be replaced with longer columns or high-efficiency spinning band columns, though these have not materially increased product purity. The particular solvents used in the process of this invention can also be varied, as for example, by replacement of the preferred methanol solvent with diethyl ether, with consequential increase in yield and decrease in product purity.

The improved process of this invention has succeeded in producing 1-methoxycycloheptatriene in substantially increased yields and purity at an increased reaction rate through use of a polymerization inhibitor/retarder for minimizing impurities and extraneous materials in the reaction product.

The improved process of this invention can further be used for synthesizing analogous alkoxycycloheptatriene isomers by substitution of the appropriate corresponding reactants in the novel process steps of this invention.

The particular polymerization inhibitor used can be selected from conventional polymerization inhibitors such as hydroquinone, nitrobenzene and L-ascorbyl palmitate, though phenothiazine has been found to give far better results in the process of this invention.

Finally, the 1-methoxycycloheptatriene synthesized by the improved process of this invention has been known in the art as an effective irritant agent which can be disseminated in liquid or vapor form by conventional dissemination means. The use of 1-methoxycycloheptatriene as an irritant agent and the method of disseminating this agent is therefore not considered a part of this invention.

Applicant having disclosed his invention, obvious modification will become apparent to those skilled in the related chemical art. Applicant therefore wishes to be limited only by the scope of the appended claims.

I claim:

1. An improved method for synthesizing the irritant 1-methoxycycloheptatriene in increased yields and purity through the steps of
   (a) reacting an aqueous solution of cycloheptatrienyl tetrafluoroborate with methanol and sodium bicarbonate to produce 7-methoxycycloheptatriene;
   (b) thermally isomerizing said 7-methoxycycloheptatriene by heating to produce an isomer product containing as its major constituent 3-methoxycycloheptatriene;
   (c) subsequently isomerizing said 3-methoxycycloheptatriene by acid catalyzed rearrangement with methanolic hydrogen chloride followed by neutralization to give a crude 1-methoxycycloheptatriene product and
   (d) filtering and fractionally distilling said crude product the improvement comprising the step of utilizing a polymerization inhibitor in at least one of the reaction steps to minimize formation of polymer impurities and thereby increase the overall yield and purity of the product 1-methoxycycloheptatriene.

2. The process of claim 1 wherein the concentration of the polymerization inhibitor is maintained at a concentration of 0.1–1.0% by weight of the reactant during all reaction steps of the process.

3. The process of claim 2 wherein the polymerization inhibitor is selected from the group consisting of phenothiazine, hydroquinone, nitrosobenzene, and L-ascorbyl palmitate.

4. The process of claim 3 wherein the polymerization inhibitor is phenothiazine.

5. The process of claim 1 wherein the thermal isomerization in step (b) is achieved by heating at 150° C. under atmospheric pressure.

6. The process of claim 5 wherein the product 1-methoxycycloheptatriene is obtained in a final yield of 62–69% by weight, based upon the reactants, and has a purity of approximately 92 mole % 1-methoxycycloheptatriene.

7. The process of claim 1 further including the improvement in step (a) of preparing the aqueous solution of cycloheptatrienyl tetrafluoroborate with water which has been purged with nitrogen and heated to approximately 52° C. to give an increased yield and purity of 7-methoxycycloheptatriene.

8. The process of claim 7 wherein the neutralization in step (c) is achieved through use of triethylamine.

9. The process of claim 1 further including the improvement in step (b) of thermally isomerizing 7-methoxycycloheptatriene to an isomer mixture containing 1-methoxycycloheptatriene as its principal constituent by heating at temperatures of at least 180° C. under pressure.

10. The process of claim 9 wherein the thermal isomerization is achieved by heating at 180° C. for 3 hours in a sealed reaction vessel.

11. The process of claim 10 wherein the final product 1-methoxycycloheptatriene is present in a yield of approximately 70–75% by weight, by upon the reactants, and has a purity of 92–93.6% 1-methoxycycloheptatriene.

12. A process for synthesizing the irritant 1-methoxycycloheptatriene comprising the steps of (a) reacting an aqueous solution of cycloheptatrienyl tetrafluoborate and phenothiazine polymerization inhibitor, with methanol and sodium bicarbonate to produce 7-methoxycycloheptatriene, (b) completely isomerizing said 7-methoxycycloheptatriene by heating at temperatures of at least 180° C. under pressure, in the presence of phenothiazine, to produce an isomer mixture consisting of a major amount of 1-methoxycycloheptatriene and minor amounts of 2-methoxy and 3-methoxycycloheptatriene, (c) isomerizing said isomer mixture by acid catalyzed rearrangement with methanolic hydrogen chloride in the presence of phenothiazine, followed by neutralization to give a crude 1-methoxycycloheptatriene product and (d) filtering and distilling said crude product to give a high yield of substantially pure 1-methoxycycloheptatriene.

13. The process of claim 12 wherein the isomerization of 7-methoxycycloheptatriene in step (b) is achieved by heating at temperatures of at least 180° C.

14. The process of claim 12 wherein the neutralization in step (c) is accomplished through use of triethylamine.

15. The process of claim 12 wherein the phenothiazine is present in a concentration of 0.1–1.0% by weight of reactants during all reaction steps of the process.

16. The process of claim 13 wherein the complete isomerization of 7-methoxycycloheptatriene is achieved by heating at 180° C. for 3 hours in a sealed reaction vessel.

17. The process of claim 16 wherein the final product yield is approximately 70–75% by weight, based upon the reactant of 1-methoxycycloheptatriene of 92–93.6 mole % purity.

* * * * *